US006410022B1

(12) United States Patent
Rittershaus

(10) Patent No.: US 6,410,022 B1
(45) Date of Patent: Jun. 25, 2002

(54) MODULATION OF CHOLESTERYL ESTER TRANSFER PROTEIN (CETP) ACTIVITY

(75) Inventor: Charles W. Rittershaus, Malden, MA (US)

(73) Assignee: Avant Immunotherapeutics, Inc., Needham, MA (US)

( * ) Notice: Subject to any disclaimer, the term of this patent is extended or adjusted under 35 U.S.C. 154(b) by 0 days.

(21) Appl. No.: 08/432,483

(22) Filed: May 1, 1995

(51) Int. Cl.$^7$ .................. A61K 39/00; A61K 39/02; C07K 19/00
(52) U.S. Cl. .................. 424/185.1; 424/190.1; 424/192.1; 424/193.1; 424/197.11; 424/236.1; 530/300; 530/324; 530/403
(58) Field of Search .................. 530/324, 300, 530/359, 403; 424/192.1, 236.1, 185.1, 190.1, 193.1, 197.11; 435/135

(56) References Cited

U.S. PATENT DOCUMENTS

| | | | |
|---|---|---|---|
| 5,242,687 A | 9/1993 | Tykocinski et al. | |
| 5,338,829 A | 8/1994 | Weiner et al. | |

FOREIGN PATENT DOCUMENTS

| | | |
|---|---|---|
| EP | 0343460 A2 | 11/1989 |
| WO | WO 90/15627 | 12/1990 |
| WO | WO 92/10203 | 6/1992 |
| WO | WO 93/11782 | 6/1993 |
| WO | WO 93/23076 | 11/1993 |
| WO | WO 94/24567 | 10/1994 |
| WO | WO 94/25060 | 10/1994 |
| WO | WO 96/39168 | 12/1996 |

OTHER PUBLICATIONS

Stevens Use of Synthetic Peptids for developing a vaccine against human chronic gonadotropin in Synthetic Vaccines vol. II Ed b. R. Aaron Boca Raton,Fl, CRC, 1987 p. 111–133.*
Albers et al., *Arteriosclerosis*, 4: 49–58 (1984).
Barter et al., *J. Lipid Res.*, 21:238–249 (1980).
Bevilacqua et al., *J. Clin. Invest.*, 91:379–387 (1993).
Bisgaier et al., *J. Lipid Res.*, 34: 1625–1634 (1993).
Bisgaier et al., *J. Lipid Res.*, 32: 21–23 (1991).
Breslow et al., *Proc. Natl. Acad. Sci. USA*, 90:8314–8318 (1993).
Brown et al., *Nature*, 342: 448–451 (1989).
Carlsson et al., *Biochem. J.*, 173: 723–737 (1978).
Casali et al., *Science*, 234: 476–479 (1986).
Castelli et al., *J. Am. Med. Assoc.*, 256: 2835–2838 (1986).
Drayna et al., *Nature*, 327: 632–634 (1987).
Eldridge et al., in *Immunobiology of Proteins and Peptides V: Vaccines: Mechanisms, Design, and Applications*, Atassi, M.Z., ed. (Plenum Press, New York, 1989), pp. 191–202.
Engelhard, Victor H., *Sci. Am.*, 54–60 (1994).
Etlinger et al., *Science*, 249: 423–425 (1990).
Etlinger, H., *Immunol. Today*, 13: 52–55 (1992).
Fielding et al., *J. Lipid Res.*, 36: 211–228 (1995).
Frondorf et al., *J. Immunol. Methods 172*: 135–137 (1994).
Gavish et al., *J. Lipid Res.*, 28: 257–267 (1987).
Gaynor et al., *Atherosclerosis*, 110: 101–109 (1994).
*Genetic Engineering News*, 14: 44 (Aug. 1994).
Gordon et al., *N. Engl. J. Med.*, 321: 1311–1316 (1989).
Green et al., *Cell*, 28: 477–487 (1982).
Ha et al., *Comp. Biochem. Physiol.*, 83B: 463–466 (1986).
Ha et al., *Biochim. Biophys. Acta*, 833: 203–211 (1985).
Havel et al., "Introduction: Structure and metabolism of plasma lipoproteins", In *The Metabolic Basis of Inherited Disease*, 6th ed., pp. 1129–1138 (Scriver, C.R., et al., eds.) (McGraw–Hill, Inc., New York, 1989).
Hayek et al., *J. Clin. Invest.*, 90: 505–510 (1992).
Hayek et al., *J. Clin. Invest.*, 91: 1665–1671 (1993).
Hesler et al., *J. Biol. Chem.*, 263: 5020–2023 (1988).
Hesler et al., *J. Biol. Chem.*, 262: 2275–2282 (1987).
Inazu et al., *N. Eng. J. Med.*, 323: 1234–1238 (1990).
Jarnagin et al., *Proc. Natl. Acad. Sci. USA*, 84: 1854–1854 (1987).
Jiang et al., *J. Biol. Chem.*, 266: 4631–4639 (1991).
Jiang et al., *J. Biol. Chem.*, 268: 27406–27412 (1993).
Kligfield et al., *Am. Heart J.*, 113:589–597 (1987).
Korn et al., *J. Mol. Biol.*, 65: 525–529 (1972).
Kushwaha et al., *J. Lipid Res.*, 34: 1285–1297 (1993).
Mader, S.S., In *Human Biology*, 4th ed., pp. 83, 102 (Wm. C. Brown Publishers, Dubuque, Iowa, 1995).
Marguerite et al., *Mol. Immunol.*, 29: 793–800 (1992).
Marotti et al., *Nature*, 364: 73–75 (1993).
Mathews, C.K. and van Holde, K.E., *Biochemistry*, pp. 574–576, 626–630 (The Benjamin/Cummings Publishing Co., Redwood City, California, 1990).
Means and Feeney (*Bioconjugate Chem.*, 1: 2–12 (1990).
Mezdour et al., *Clin. Chem.* 40/4: 593–597 (1994).
Nagashima et al., *J. Lipid Res.*, : 1643–6149 (1988).
Nelson et al., *J. Clin. Invest.*, 91: 1157–1166 (1993).
Palker et al., *Proc. Natl. Acad. Sci. USA*, 84: 2479–2483 (1987).
Panina–Bordignon et al., *Eur. J. Immunol.*, 19: 2237–2242 (1989).
*Physician's Desk Reference*, 49th ed., (Medical Economics Data Production Co., Montvale, New Jersey, 1995), pp. 1628, 2371 (referring to hepatitis B vaccine), pp. 1501, 1573, 1575 (referring to measles, mumps, and/or rubella vaccines), pp. 904, 919, 1247, 1257, 1289, 1293, 2363 (referring to diphtheria, tetanus and/or pertussis vaccines).
Pruitt et al., *Transplantations*, 52: 868–873 (1991).
Pruitt et al., *J. Surg. Res.*, 50: 350–355 (1991).

(List continued on next page.)

*Primary Examiner*—David Saunders
(74) *Attorney, Agent, or Firm*—Thomas R. Berka; Leon R. Yankwich

(57) ABSTRACT

This invention relates to peptides comprising a helper T cell epitope portion and a B cell epitope portion for eliciting an immune response against endogenous cholesteryl ester transfer protein (CETP) activity, to prevent or treat cardiovascular disease, such as atherosclerosis.

26 Claims, 6 Drawing Sheets

OTHER PUBLICATIONS

Quig et al., *Ann. Rev. Nutr.,* 10: 169–193 (1990).
Quinet et al., *J. Clin. Invest.,* 85: 357–363 (1990).
Rye et al., *J. Biol. Chem.,* 270: 189–196 (1995).
Sad et al., *Immunol.,* 76: 599–603 (1992).
Sambrook et al., *Molecular Cloning: A Laboratory Manual,* vols. 1–3 (Cold Spring Harbor Laboratory, Cold Spring Harbar, New York, 1989).
*Science,* 262: 1974–1975 (1993).
Suckling, Keith E., *Bio/Technology,* 12: 1379–1380 (1994).
Swenson et al., *J. Biol. Chem.,* 264: 14318–14326 (1989).
Swenson et al., *J. Biol. Chem.,* 263: 5150–5157 (1988).
*Synthetic Vaccines,* Nicholson, B.H., ed. (Blackwell Scientific Publications, Cambridge, Massachusetts, 1994), pp. 236–238.
Tall, A.R. *J. Lipid Res.,* 34: 1255–1274 (1993).
Tall, A.R., *J. Clin. Invest.,* 89:379–384 (1990).
Tall, A.R., *J. Internal Med.,* 237: 5–12 (1995).
Talwar et al., *Proc. Natl. Acad. Sci. USA,* 91: 8532–8536 (1994).
Tam, J..P., *Proc. Natl. Acad. Sci. USA,* 85: 5409–5413 (1988).
Tao et al., *Nature,* 362: 755–758 (1993).
Tato et al., *Arterioscler. Thromb. Vascular Biol.,* 15: 112–120 (1995).
Valmori et al., *J. Immunol.,* 149: 717–721 (1992).
Wang et al., *J. Biol. Chem.,* 270: 612–618 (1985).
Wang et al., *Science,* 254: 285–288 (1991).
Wang et al., *J. Biol. Chem.,* 268: 1955–1959 (1993).
Wang et al., *J. Biol. Chem.,* 267: 17487–17490 (1992).
Watanabe et al., *Proc. Natl. Acad. Sci. USA,* 89: 5103–5107 (1992).
Wedrychowski et al., *Biotechnology,* 11(4): 486–489 (1993).
Weisman et al., *Science,* 249: 146–151 (1990).
Whitlock et al., *J. Clin. Invest.,* 84: 129–137 (1989).
Yeh et al., *J. Immunol.,* 146: 250–256 (1991).
Yen et al., *J. Clin. Invest.,* 83: 2018–2024 (1989).
Zannis et al., "Genetic mutations affecting human lipoproteins, their receptors, and their enzymes", In *Advances in Human Genetics,* vol. 21, pp. 145–319 (Plenuma Press, New York, 1993).
Zegers et al., *Eur. J. Immunol* 23: 630–634 (1993).

* cited by examiner

FLOW CHART

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH:   2 6 amino acids
      (B) TYPE:     amino acid
      (D) TOPOLOGY: linear (ii) MOLECULE TYPE:    peptid e (iii) HYPOTHETICAL:

(iv) ANTI-SENSE:

(ix) FEATURE:
      (A) NAME/KEY: Carboxyl terminal 26 amino acids of
         human CE TP
      (B) LOCATION:

(x) PUBLICATION INFORMATION:
      (A) AUTHORS: Drayna, D ennis, et al.
      (B) TITLE: Cloning and  sequencing of human

```
            cholesteryl  ester transfer cDNA
       (C) JOURNAL: Nature
       (D) VOLUME: 327
       (E) ISSUE:
       (F) PAGES: 632-634
       (G) DATE: 18-JUN-1987
       (K) RELEVANT RESIDUES IN SEQ ID NO:1:FROM 1 TO 26

(xi) SEQUENCE DESCRIPTION: SEQ ID NO: 1:

Arg Asp Gly Phe Leu Leu Leu Gln Met Asp Phe
1               5                   10

Gly Phe Pro Glu His Leu Leu Val Asp Phe Leu
            15              20

Gln Ser Leu Ser
        25

(2) INFORMATION FOR SEQ ID NO:2:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (iii) HYPOTHETICAL:

(iv) ANTI-SENSE:

(ix) FEATURE:
        (A) NAME/KEY:
        (B) LOCATION:

(xi) SEQUENCE DESCRIPTION: SEQ ID NO: 2:

Cys Gln Tyr Ile Lys Ala Asn Ser Lys Phe Ile
1               5                   10

Gly Ile Thr Glu Phe Gly Phe Pro Glu His Leu
            15              20

Leu Val Asp Phe Leu Gln Ser Leu Ser
            25              30

(2) INFORMATION FOR SEQ ID NO:3:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (iii) HYPOTHETICAL:

(iv) ANTI-SENSE:

(ix) FEATURE:
        (A) NAME/KEY: 21-amino acid tetanus toxoid universal
            helper T  cell epitope.
        (B) LOCATION:

(x) PUBLICATION INFORMATION:
        (A) AUTHORS: Panina-Bordi gnon, P., et al.
        (B) TITLE: Universally immunogenic T cell
            epitopes: promiscuous binding to human MHC class II and
            promiscuous  recognition by T cells
        (C) JOURNAL: European Journal of Immunology
        (D) VOLUME: 19
        (E) ISSUE:
        (F) PAGES: 2237-2242
        (G) DATE: 1989
        (K) RELEVANT RESIDUES IN SEQ ID NO:3:FROM 1 TO 21
```

-continued (xi) SEQUENCE DESCRIPTION: SEQ ID NO: 3:

Phe Asn Asn Phe Thr Val Ser Phe Trp Leu Arg
1               5                   10
Val Pro Lys Val Ser Ala Ser His Leu Glu
            15                  20

(2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL:

(iv) ANTI-SENSE:

(ix) FEATURE:
        (A) NAME/KEY: 6 amino acids of lipophilic peptide
            adjuvant Pam3-Cys-Ser-Lys4.
        (B) LOCATION:

(xi) SEQUENCE DESCRIPTION: SEQ ID NO:4:

Cys Ser Lys Lys Lys Lys
1               5

(2) INFORMATION FOR SEQ ID NO:5:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL:

(iv) ANTI-SENSE:

(ix) FEATURE:
        (A) NAME/KEY: 6 amino acids of lipophilic peptide
            adjuvant Pam3-Cys-Ser-Glu4.
        (B) LOCATION:

(xi) SEQUENCE DESCRIPTION: SEQ ID NO:5:

Cys Ser Glu Glu Glu Glu
1               5

MODULATION OF CHOLESTERYL ESTER TRANSFER PROTEIN (CETP) ACTIVITY

GENERAL FIELD OF THE INVENTION

This invention is generally in the field of peptide-based vaccines to control atherogenic activity in the circulatory system of humans and other animals. In particular, this invention provides compositions and methods for providing endogenous means to inhibit the activity of endogenous cholesteryl ester transfer protein (CETP) and to effectively modulate the relative levels of lipoproteins to produce a condition correlated with a reduced risk of cardiovascular disease, such as atherosclerosis.

BACKGROUND OF THE INVENTION

Cholesterol circulates through the body predominantly as components of lipoprotein particles (lipoproteins), which are composed of a protein portion, called apolipoproteins (Apo) and various lipids, including phospholipids, triglycerides, cholesterol and cholesteryl esters. There are ten major classes of apolipoproteins: Apo A-I, Apo A-II, Apo-IV, Apo B-48, Apo B-100, Apo C-I, Apo C-II, Apo C-III, Apo D, and Apo E. Lipoproteins are classified by density and composition. For example, high density lipoproteins (HDL), one function of which is to mediate transport of cholesterol from peripheral tissues to the liver, have a density usually in the range of approximately 1.063–1.21 g/ml. HDL contain various amounts of Apo A-I, Apo A-II, Apo C-I, Apo C-II, Apo C-III, Apo D, Apo E, as well as various amounts of lipids, such as cholesterol, cholesteryl esters, phospholipids, and triglycerides.

In contrast to HDL, low density lipoproteins (LDL), which generally have a density of approximately 1.019–1.063 g/ml, contain Apo B-100 in association with various lipids. In particular, the amounts of the lipids cholesterol and cholesteryl esters are considerably higher in LDL than in HDL, when measured as a percentage of dry mass. LDL are particularly important in delivering cholesterol to peripheral tissues.

Very low density lipoproteins (VLDL) have a density of approximately 0.95–1.006 g/ml and also differ in composition from other classes of lipoproteins both in their protein and lipid content. VLDL generally have a much higher amount of triglycerides (TG) than do HDL or LDL and are particularly important in delivering endogenously synthesized triglycerides from liver to adipose and other tissues. The features and functions of various lipoproteins have been reviewed (see, for example, Mathews, C. K. and van Holde, K. E., *Biochemistry*, pp. 574–576, 626–630 (The Benjamin/Cummings Publishing Co., Redwood City, Calif., 1990); Havel, R. J., et al., et al., "Introduction: Structure and metabolism of plasma lipoproteins", In *The Metabolic Basis of Inherited Disease*, 6th ed., pp. 1129–1138 (Scriver, C. R., et al., eds.) (McGraw-Hill, Inc., New York, 1989); Zannis, V. I., et al., "Genetic mutations affecting human lipoproteins, their receptors, and their enzymes", In *Advances in Human Genetics* Vol. 21, pp. 145–319 (Plenum Press, New York, 1993)).

Decreased susceptibility to cardiovascular disease, such as atherosclerosis, is generally correlated with increased absolute levels of circulating HDL and also increased levels of HDL relative to circulating levels of lower density lipoproteins such as VLDL and LDL (see, e.g., Gordon, D. J., et al., *N. Engl. J. Med.*, 321: 1311–1316 (1989); Castelli, W. P., et al., *J. Am. Med. Assoc.*, 256: 2835–2838 (1986); Miller, N. E., et al., *Am. Heart J.*, 113: 589–597 (1987); Tall, A. R, *J. Clin. Invest.*, 89: 379–384 (1990); Tall, A. R., *J. Internal Med*, 237: 5–12 (1995)).

Cholesteryl ester transport protein (CETP) mediates the transfer of cholesteryl esters from HDL to TG-rich lipoproteins such as VLDL and LDL, and also the reciprocal exchange of TG from VLDL to HDL (Tall, A. R., *J. Internal Med.*, 237: 5–12 (1995); Tall, A. R., *J. Lipid Res.*, 34: 1255–1274 (1993); Hesler, C. B., et al., *J. Biol. Chem.*, 262: 2275–2282 (1987); Quig, D. W. et al., *Ann. Rev. Nutr.*, 10: 169–193 (1990)). CETP may play a role in modulating the levels of cholesteryl esters and TG associated with various classes of lipoproteins. A high CETP cholesteryl ester transfer activity has been correlated with increased levels of LDL-associated cholesterol and VLDL-associated cholesterol, which in turn are correlated with increased risk of cardiovascular disease (see, e.g., Tato, F., et al., *Arterioscler. Thromb. Vascular Biol.*, 15: 112–120 (1995)).

Hereinafter, LDL-C will be used to refer to total cholesterol, including cholesteryl esters and/or unesterified cholesterol, associated with low density lipoprotein. VLDL-C will be used to refer to total cholesterol, including cholesteryl esters and/or unesterified cholesterol associated with very low density lipoprotein. HDL-C will be used to refer to total cholesterol, including cholesteryl esters and/or unesterified cholesterol, associated with high density lipoprotein.

CETP isolated from human plasma is a hydrophobic glycoprotein having 476 amino acids and a molecular weight of approximately 66,000 to 74,000 daltons on sodium dodecyl sulfate (SDS)-polyacrylamide gels (Albers, J. J., et al., *Arteriosclerosis*, 4: 49–58 (1984); Hesler, C. B., et al., *J. Biol. Chem.*, 262: 2275–2282 (1987); Jarnagin, S. S., et al., *Proc. Natl. Acad. Sci. USA*, 84: 1854–1857 (1987)). A cDNA encoding human CETP has been cloned and sequenced (Drayna, D., et al., *Nature*, 327: 632–634 (1987)). CETP has been shown to bind CE, TG, phospholipids (Barter, P. J. et al., *J. Lipid Res.*, 21:238–249 (1980)), and lipoproteins (see, e.g., Swenson, T. L., et al., *J. Biol. Chem.*, 264: 14318–14326 (1989)). More recently, the region of CETP defined by the carboxyl terminal 26 amino acids, and in particular amino acids 470 to 475, has been shown to be especially important for neutral lipid binding involved in neutral lipid transfer (Hesler, C. B., et al., *J. Biol. Chem.*, 263: 5020–5023 (1988)), but not phospholipid binding (see, Wang, S., et al., *J. Biol. Chem.*, 267: 17487–17490 (1992); Wang, S., et al., *J. Biol. Chem.*, 270: 612–618 (1995)).

A monoclonal antibody (Mab), TP2 (formerly designated 5C7 in the literature), has been produced which inhibits completely the cholesteryl ester and TG transfer activity of CETP, and to a lesser extent the phospholipid transfer activity (Hesler, C. B., et al., *J. Biol. Chem.*, 263: 5020–5023 (1988)). The epitope of TP2 was localized to the carboxyl terminal 26 amino acids, i.e., the amino acids from arginine-451 to serine-476, of the 74,000 dalton human CETP molecule (see, Hesler, C. B., et al., (1988)). TP2 was reported to inhibit CETP activity in human plasma in vitro (Yen, F. T., et al., *J. Clin. Invest.*, 83: 2018–2024 (1989)). Further analysis of the region of CETP bound by TP2 revealed that amino acids between phenylalanine-463 and leucine-475 are necessary for TP2 binding and for neutral lipid (e.g., cholesteryl ester) transfer activity (see, Wang, S., et al., 1992).

A number of in vivo studies utilizing animal models or humans have indicated that CETP activity can affect the level of circulating cholesterol-containing HDL. Increased CETP cholesteryl ester transfer activity can produce a decrease in HDL-C levels relative to LDL-C and/or VLDL-C (where HDL-C, LDL-C, and VLDL-C refer generally to cholesteryl ester and/or unesterified cholesterol associated with HDL, LDL, and VLDL, respectively) levels which in turn is correlated with an increased susceptibility to atherosclerosis. Injection of partially purified human CETP into rats (which normally lack CETP activity), resulted in a shift of cholesteryl ester from HDL to VLDL, consistent with CETP-promoted transfer of cholesteryl ester from HDL to VLDL (Ha, Y. C., et al., Biochim. Biophys. Acta, 833: 203–211 (1985); Ha, Y. C., et al., Comp. Biochem. Physiol., 83B: 463–466 (1986); Gavish, D., et al., J. Lipid Res., 28: 257–267 (1987)). Transgenic mice expressing human CETP were reported to exhibit a significant decrease in the level of cholesterol associated with HDL (see, e.g., Hayek, T., et al., J. Clin. Invest., 90: 505–510 (1992); Breslow, J. L., et al., Proc. Natl. Acad. Sci. USA, 90: 8314–8318 (1993)). Furthermore, whereas wild-type mice are normally highly resistant to atherosclerosis (Breslow, J. L., et al., Proc. Natl. Acad. Sci. USA, 90: 8314–8318 (1993)), transgenic mice expressing a simian CETP were reported to have an altered distribution of cholesterol associated with lipoproteins, namely, elevated levels of LDL-C and VLDL-C and decreased levels of HDL-C (Marotti K. R., et al., Nature, 364: 73–75 (1993)). Transgenic mice expressing simian CETP also were susceptible to dietary-induced severe atherosclerosis compared to non-expressing control mice (Marotti et al., id.). Intravenous infusion of anti-human CETP monoclonal antibodies (Mab) into hamsters and rabbits inhibited CETP activity in vivo and resulted in significantly increased levels of HDL-C levels, decreased levels of HDL-TG, and increased HDL size; again implicating a critical role for CETP in the distribution of cholesterol in circulating lipoproteins (Gaynor, B. J., et al., Atherosclerosis, 110: 101–109 (1994) (hamsters); Whitlock, M. E., et al., J. Clin. Invest., 84: 129–137 (1989) (rabbits)).

CETP deficiency has also been studied in humans. For example, in certain familial studies in Japan, siblings that were homozygous for non-functional alleles of the CETP gene had no detectable CETP activity. Virtually no atherosclerotic plaques were exhibited by these individuals, who also showed a trend toward longevity in their families (see, e.g., Brown, M. L., et al., Nature, 342: 448–451 (1989); Inazu, A., et al., N. Engl. J. Med., 323: 1234–1238 (1990); Bisgaier, C. L., et al., J. Lipid Res., 32: 21–23 (1991)). Such homozygous CETP-deficient individuals also were shown to have an anti-atherogenic lipoprotein profile as evidenced by elevated levels of circulating HDL rich in cholesteryl ester, as well as overall elevated levels of HDL, and exceptionally large HDL, i.e., up to four to six times the size of normal HDL (Brown, M. L., et al., 1989, p. 451). The frequency of this mutation in Japan is relatively high, and may account for an elevated level of HDL in a significant fraction of the Japanese population.

The above studies indicate that CETP plays a major role in transferring cholesteryl ester from HDL to VLDL and LDL, and thereby in altering the relative profile of circulating lipoproteins to one which is associated with an increased risk of cardiovascular disease (e.g., decreased levels of HDL-C and increased levels of VLDL-C and LDL-C). Taken together, the current evidence suggests that increased levels of CETP activity may be predictive of increased risk of cardiovascular disease. Modulation or inhibition of endogenous CETP activity is thus an attractive therapeutic method for modulating the relative levels of lipoproteins to reduce or prevent the progression of or to induce regression of cardiovascular diseases, such as atherosclerosis.

It would be advantageous, therefore, to discover compounds and methods to control CETP activity which would be helpful in preventing or treating cardiovascular disease. To be an effective pharmacological therapeutic, a compound when administered to a significant majority of recipients, ideally, would not elicit an immune response which neutralizes the beneficial activity or effect of the therapeutic compound, must not promote a hypersensitive state in the individual receiving the therapeutic compound, and must not produce untoward side effects. It would also be advantageous if such compounds and methods avoided the necessity for continuous or frequently repeated treatments.

SUMMARY OF THE INVENTION

This invention provides compounds and methods useful for the modulation or inhibition of cholesteryl ester transfer protein (CETP) activity. In particular, vaccine peptides are described which, when administered to a mammal, raise an antibody response against the mammal's own endogenous CETP. Such vaccine peptides comprise a helper T cell epitope portion comprising a universal immunogenic helper T cell epitope, linked, preferably covalently, to a B cell epitope portion comprising a carboxyl terminal portion of human CETP protein that is involved in a neutral lipid binding or a transfer activity of CETP. In a preferred embodiment, the helper T cell epitope portion of a vaccine peptide of this invention is derived from an amino acid sequence of a universally immunogenic helper T cell epitope, such as those found in tetanus and diptheria toxoids, or in antigenic peptides known from pertussis vaccine, Bacile Calmette-Guerin (BCG), polio vaccine, measles vaccine, mumps vaccine, rubella vaccine, purified protein derivative (PPD) of tuberculin, and keyhole limpet hemocyanin. Furthermore, various universal antigenic helper T cell epitopes may be linked to one another to form multiple universal antigenic helper T cell epitope portions of the vaccine peptides of this invention. In a more preferred embodiment of a vaccine peptide of this invention, an amino terminal cysteine residue is covalently linked to an amino acid sequence of a universal antigenic helper T cell epitope of tetanus toxoid forming the sequence C Q Y I K A N S K F I G I T E (amino acids 1 to 15 of SEQ ID NO:2), which is covalently linked to a B cell epitope portion of a vaccine peptide having the carboxyl terminal CETP amino acid sequence F G F P E H L L V D F L Q S L S (amino acids 16 to 31 of SEQ ID NO:2).

The peptides of this invention may also be linked to a common molecule to form peptide assemblies in which multiple copies of the peptides are arranged close to one another. Such multicopy (or multivalent) peptide assemblies may be more immunogenic, that is, produce a more effective immune response to endogenous CETP than vaccines comprising unassociated individual peptides. The vaccine compounds of this invention also may be used in combination with a pharmaceutically acceptable adjuvant.

The immunogenic vaccine peptides of this invention elicit the production of antibodies that are reactive with or recognize CETP. Administration of vaccine peptides to test animals resulted in a decline in the relative levels of total cholesterol and HDL-C. The elicited endogenous anti-CETP antibodies may promote a physiological condition correlated with decreased risk of cardiovascular disease, such as atherosclerosis.

DETAILED DESCRIPTION OF THE INVENTION

Figure 1:
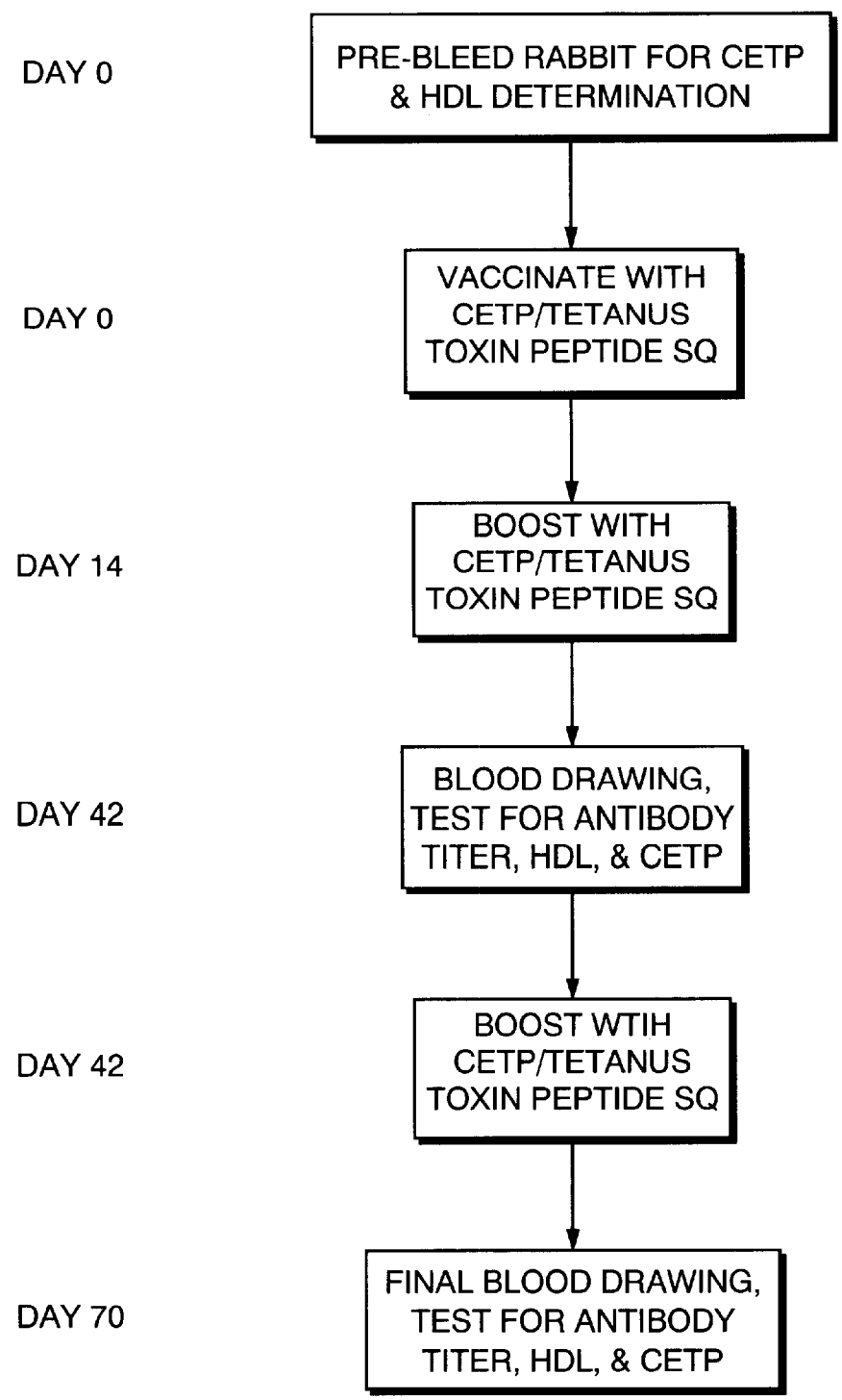
FIG. 1. Flow chart of the protocol for administration of a vaccine peptide to (vaccination of) rabbits and for withdrawing blood samples for analysis of vaccine efficacy. A control rabbit received no vaccine peptide.

As noted above, a decreased risk of cardiovascular disease, such as atherosclerosis, has been correlated with relatively low circulating levels of LDL and VLDL and relatively high levels of HDL. The levels of such circulating lipoproteins are directly influenced, at least in part, by the endogenous levels of CETP activity. In particular, high CETP activity promotes transfer of neutral lipids, such as cholesteryl esters from HDL to VLDL and LDL. Accordingly, CETP is a relatively precise target in humans and other animals for altering the relative levels of LDL, VLDL and HDL in the circulatory system (see, e.g., Tato, F., et al., *Arteriosclero. Thromb. Vascular Biol.*, 15: 112–120 (1995); Tall, A. R., *J. Internal Med.*, 237: 5–12 (1995)). This invention is directed to the control of endogenous CETP activity by providing CETP vaccine peptides useful for promoting an immune response in individuals against their endogenous CETP, thereby promoting a physiological condition, e.g., increased level of HDL or decreased level of LDL, correlated with a decreased risk of cardiovascular disease.

1. Peptides and Compositions for Modulation of CETP Activity

As used herein, a CETP vaccine peptide is a peptide comprising a helper T cell epitope portion comprising an amino acid sequence of a universal antigenic helper T cell epitope and a B cell epitope portion comprising an amino acid sequence of a carboxyl terminal region of CETP involved in neutral lipid binding and/or neutral lipid transfer activity. Such CETP vaccine peptides are antigenic, that is, they elicit production of specific antibodies for that peptide which bind endogenous CETP. Thus, the CETP vaccine peptides of this invention are immunogenic moieties that have the capacity to stimulate the formation of antibodies which specifically bind endogenous CETP and/or inhibit endogenous CETP activity.

A. Helper T Cell Epitope Portion of Vaccine Peptides

Peptides useful in the compositions and methods of this invention comprise a helper T cell epitope portion and a B cell epitope portion. The helper T cell epitope portion has an amino acid sequence of a universal antigenic (or universal immunogenic) helper T cell epitope (also called an immunogenic carrier peptide), which is defined as a peptide, or derivative thereof, which can be presented by multiple major histocompatibility complex (MHC) haplotypes and thereby activate helper T cells, which in turn, stimulate B cell growth and differentiation. The B cell epitope portion (also called a CETP-related peptide portion) has an amino acid sequence comprising a portion of the carboxyl terminal region of the enzyme CETP that is involved in neutral lipid binding and/or neutral lipid transfer.

Examples of universal antigenic helper T cell epitopes which have been used as immunogenic carrier peptides for human vaccination are known in the art. These include, for example, epitopes of tetanus toxoid (tt) and diptheria toxoid (dt) (see, e.g., Panina-Bordignon, P., et al., *Eur. J. Immunol.*, 19: 2237–2242 (1989) (characterization of universal tetanus toxoid helper T cell epitope peptides); Etlinger, H., *Immunol. Today*, 13: 52–55 (1992); Valmori, D., et al., *J. Immunol.*, 149: 717–721 (1992) (use of universal tt epitopes in candidate anti-malarial vaccine); Talwar, G. P., et al., *Proc. Natl. Acad. Sci. USA*, 91: 8532–8536 (1994) (use of tt and dt as universal epitopes in anti-human chorionic gonadotropin vaccine); Talwar, G. P., et al., *Proc. Natl. Acad. Sci. USA*, 91: 8532–8536 (1994)). In addition to tt and dt, other T cell epitope sequences useful in this invention include those derived from antigenic peptides known from pertussis vaccine, Bacile Calmette-Guerin (BCG), polio vaccine, measles vaccine, mumps vaccine, rubella vaccine, and purified protein derivative (PPD) of tuberculin (see, e.g., Etlinger, H., *Immunol. Today*, 13: 52–55 (1992)); incorporated herein by reference). Furthermore, various universal antigenic helper T cell epitopes may be linked to one another to form multiple helper T cell epitope portions of the vaccine peptides of this invention. For example, a vaccine peptide of this invention can be synthesized containing a multiple helper T cell epitope portion comprising an amino acid sequence of a tt helper T cell epitope and a dt helper T cell epitope. In addition, immunogenicity of a vaccine peptide of this invention may be further enhanced by linking the helper T cell epitope portion to a peptide sequence of a xenogeneic CETP or a related protein homologous to CETP. Such an approach was used previously in a human vaccine to human chorionic gonadotropin (see, Talwar, G. P., et al., *Proc. Natl. Acad. Sci. USA.*, 91: 8532–8536 (1994); heterospecies dimer formed between an amino acid sequence from β subunit of human chorionic gonadotropin and an amino acid sequence of α subunit of ovine luteinizing hormone). Examples of proteins related to CETP that might be used in this approach include, for example, phospholipid transfer protein and neutrophil bacteriocidal protein (see, Day, J. R., et al., *J. Biol. Chem.*, 269: 9388–91 (1994); Gray, P. W., et al., *J. Biol. Chem.*, 264: 9505–09 (1989)). Other immunogenic carrier molecules such as keyhole limpet hemocyanin (KLH) may also be used alone or in combination with other universal antigenic helper T cell epitopes. Preferably, the helper T cell epitope portion of the vaccine peptides of this invention comprises a universal antigenic tt or dt helper T cell epitope. In a more preferred embodiment, the peptides of this application use universal antigenic tt helper T cell epitopes having amino acid sequences Q Y I K A N S K F I G I T E (amino acids 2 to 15 of SEQ ID NO:2) and F N N F T V S F W L R V P K V S A S H L E (SEQ ID NO:3). Most preferably, the peptides of this invention use the universal antigenic tt helper T cell epitope having the amino acid sequence Q Y I K A N S K F I G I T E (amino acids 2 to 15 of SEQ ID NO:2).

B. B Cell Epitope (CETP-Related) Portion of Vaccine Peptides

The B cell epitope portion of the vaccine peptides of this invention comprise the carboxyl terminal 26 amino acids of human CETP (see SEQ ID NO:1) or fragments thereof that retain a conformation or an activity of the carboxyl terminal 26 amino acid region of CETP, e.g., fragments of the CETP carboxyl terminus which are at least six consecutive amino acids in length and which are involved in specific neutral lipid binding and/or specific neutral lipid transfer activity of CETP. More preferably, the B cell epitope (or CETP-related) portion of the vaccine peptides of this invention is any fragment of the carboxyl terminal region of CETP which is at least eleven consecutive amino acids in length, which retains the conformation of the carboxyl terminal 26 amino acid region of CETP, and which is involved in the neutral lipid binding and/or transfer activity of CETP (see, e.g., Wang, S., et al., *J. Biol. Chem.*, 267: 17487–17490 (1992); Wang, S., et al., *J. Biol. Chem.*, 268: 1955–1959 (1993)). Alternatively, the B cell epitope portion is a derivative of the carboxyl terminal 26 amino acid region of CETP containing amino acid changes (deletions, additions or substitutions) that do not significantly alter or destroy the neutral lipid binding or transfer activity of CETP (see, Wang et al., id, (1992); Wang et al., id., (1993)). Such changes in the amino acid sequence of a targeted endogenous CETP include, but are not limited to, what are generally known as conservative amino acid substitutions, such as substituting an amino acid of the CETP sequence with another of similar structure, charge, or hydrophobicity. Any addition or substitution to the CETP sequence that maintains neutral lipid binding and/or transfer activity, but improves stability in vivo or in situ, improves purification, or provides cross-linking sites (e.g., via cysteine—cysteine disulfide bond formation) is also useful in the design of a vaccine peptide of this invention.

Because CETP-mediated transfer of neutral lipids necessarily requires binding of the neutral lipid, portions of the amino acid sequence of CETP that are involved in neutral lipid binding are also useful in designing the vaccine peptides of this invention. Some portions of the amino acid sequence of CETP used to design the vaccine peptides of this invention may be involved in both neutral lipid binding as well as the actual catalytic neutral lipid transfer site of CETP. Also useful are amino acid sequences of at least six consecutive, and more preferably of at least eleven consecutive, amino acids in length of the carboxyl terminal 26 amino acid region of CETP encoded by any naturally occurring polymorphisms of the CETP gene.

Methods for testing CETP molecules for neutral lipid binding or their effect on neutral lipid transfer activity are well known in the art, (see, e.g., Swenson, T. L., et al., *J. Biol. Chem.*, 263: 5150–5157 (1988) (assay for lipid binding); Hesler, C. B., et al., *J. Biol. Chem.*, 262: 2275–2282 (1987) (assay for lipid transfer); Bisgaier, C. L., et al., *J. Lipid Res.*, 34: 1625–1634 (1993) (use of fluorescent cholesteryl ester microemulsions in CETP-mediated cholesteryl transfer activity assay); Gaynor, B. J., et al., *Atherosclerosis*, 110: 101–109 (1994) (assay for CETP lipid transfer); Wang et al. (1992) (assaying deletion mutants of CETP for transfer activity); Wang et al., (1993) (assaying single amino acid mutant forms of CETP); incorporated herein by reference). Assays for the transfer activity of CETP are also commercially available (e.g., CETP functional assay by Diagnescent Technologies, Yonkers, N.Y.).

Preferably, the B cell epitope portion of the CETP vaccine peptides of this invention comprises the amino acid sequence F G F P E H L L V D F L Q S L S (amino acids 16 to 31 of SEQ ID NO:2).

C. Production of Vaccine Peptides

The helper T cell epitope and the B cell epitope (CETP-related) portions of the CETP vaccine peptides of this invention are linked together to form immunogenic moieties. The helper T cell epitope and B cell epitope portions may be covalently linked, directly or via a cross-linking molecule. Where cross-linking molecules are used, they must join the helper T cell epitope and B cell epitope portions of the vaccine peptide together, without making the peptide toxic or significantly interfering with or reducing the overall immunogenicity of the vaccine peptide. Suitable cross-linking molecules include amino acids, for example, using one or more glycine residues to form a "glycine bridge" between the helper T cell epitope and B cell epitope portions of the vaccine peptides of this invention, disulfide bonds between cysteine residues that have been added to the helper T cell epitope and B cell epitope portions, and cross-linking molecules such as glutaraldehyde (Korn, A. H., et al., *J. Mol. Biol.*, 65: 525–529 (1972)) and other bifunctional cross-linker molecules to link a helper T cell epitope portion to a B cell epitope portion. Bifunctional cross-linker molecules possess two distinct reactive sites, one of the sites can be attached to a helper T cell epitope portion and the other to a B cell epitope portion. General methods for cross-linking molecules are reviewed by Means and Feeney (*Bioconjugate Chem.*, 1: 2–12 (1990)).

Homobifunctional cross-linker molecules have two reactive sites which are chemically the same. Examples of homobifunctional cross-linker molecules include glutaraldehyde; N,N'-bis(3-maleimido-propionyl)-2-hydroxy- 1,3-propanediol (a sulfhydryl-specific homobifunctional cross-linker); certain N-succinimide esters, such as disuccinimidyl suberate and dithio-bis-(succinimidyl propionate) and their soluble bis-sulfonic acids and salts (e.g., as available from Pierce Chemicals, Rockford, Ill.; Sigma Chemical Co., St. Louis, Mo.). For this embodiment, the relative concentrations of helper T cell epitope and B cell epitope portions should be adjusted to maximize the number of helper T cell epitope and B cell epitope portions that are linked together and to minimize the linking of identical epitope portions to each other (i.e., to avoid, for example, helper T cell epitope-helper T cell epitope or B cell epitope-B cell epitope homodimer formation).

Preferably, the bifunctional cross-linker molecule is a heterobifunctional linker molecule, meaning that the linker molecule has at least two reactive sites that can be separately activated. Use of such heterobifunctional linker molecules permits chemically separate and stepwise addition (vectorial conjugation) of each of the reactive sites of the linker molecule to the helper T cell and B cell epitope portions of the vaccine peptide. Such cross-linker molecules which may be used to link helper T cell epitope and B cell epitope portions to each other include m-maleimidobenzoyl-N-hydroxysuccinimide ester (Green, N., et al., *Cell*, 28: 477–487 (1982), cross-linking influenza viral peptides to KLH via cysteine residues in the peptides; Palker et al., *Proc. Natl. Acad. Sci. USA*, 84: 2479–2483 (1987), cross-linking a synthetic HIV gp 120 peptide to bovine serum albumin); m-maleimido-benzoylsulfosuccinimide ester; γ-maleimidobutyric acid N-hydroxysuccinimide ester; and N-succinimidyl 3-(2-pyridyl-dithio)propionate; (Carlsson, J., et al., *Biochem. J.*, 173: 723–737 (1978); Sigma Chemical Co., St. Louis, Mo.).

Furthermore, the helper T cell epitope and B cell epitope portions may be linked to a common carrier molecule, such as serum albumin or a resin or polymeric bead. Linking helper T cell epitope and B cell epitope portions to a common carrier may be accomplished using a cross-linker molecule such as glutaraldehyde or other bifunctional cross-linker molecule (see above). For this embodiment, the relative concentrations of helper T cell epitope portion, B cell epitope portion and the common carrier molecule should be adjusted to maximize the number of helper T cell epitope and B cell epitope portions that are liked to the common carrier and to minimize both the linking of identical molecules to each other (i.e., homodimer formation) and the linking of helper T cell epitope and B cell epitope portions to one another (i.e., heterodimer formation). Linking the helper T cell epitope and B cell epitope portions to another molecule or surface (e.g., the surface of a resin or polymer bead) should not significantly disrupt or reduce the immunogenic characteristics of the universal antigenic helper T cell epitope portion or of the B cell epitope (CETP-related) portion sequences. The net effect of using such bifunctional cross-linker molecules is that multiple copies of helper T cell epitope and B cell epitope portions of a vaccine peptide are bound to a common carrier which may enhance an immune response and the production of antibodies that bind to endogenous CETP. Multiple antigenic peptide arrangements have also been demonstrated to be highly effective antigens and immunogens (see, e.g., Tam, J. P., *Proc. Natl. Acad. Sci. USA*, 85: 5409–5413 (1988); Wang, C. Y., et al., *Science*, 254: 285–288 (1991); Marguerite, M., et al., *Mol. Immunol.*, 29: 793–800 (1992)).

Preferably, the helper T cell epitope and B cell epitope portions of the vaccine peptides of this invention are covalently linked end-to-end to form a continuous peptide. Most preferably, a selected universal antigenic helper T cell epitope portion forms the amino terminal portion of the vaccine peptide with its carboxyl terminal amino acid residue covalently linked in a peptide bond to the amino terminal amino acid of a selected CETP-related amino acid sequence (B cell epitope portion) of the vaccine peptide. However, the reverse order may also be used, i.e., the CETP-related amino acid sequence (B cell epitope portion) of the vaccine peptides of this invention may be positioned to form the amino terminal region of a vaccine peptide and a universal antigenic helper T cell epitope or immunogenic carrier amino acid sequence may comprise the carboxyl terminal portion of the vaccine peptide.

The peptides of this invention can be produced by any of the available methods known in the art to produce peptides of defined amino acid sequence. For example, automated peptide synthesis is available to those skilled in the art by using automated peptide synthesizers (e.g., SYNERGY Peptide Synthesizer by Applied Biosystems; AMS 422 by Abimed, Langenfeld, Germany). Synthesis of such peptides to order is performed as a commercial service by many commercial peptide synthesizing service companies, e.g., Quality Controlled Biochemicals, Inc., Hopkinton, Mass.); Chiron Mimotopes Peptide Systems (San Diego, Calif.); Bachem Bioscience, Inc. (Philadelphia, Pa.); Severn Biotech Ltd. (Kidderminster, England).

Alternatively, the peptides of this invention may be produced using synthetic and recombinant nucleic acid technology. For example, one of ordinary skill in the art can design from the known genetic code a 5' to 3' nucleic acid sequence encoding a peptide of this invention. A DNA molecule containing the coding sequences of the helper T cell epitope and B cell epitope portions (and any linking peptide, such as polyglycine, or other additional residue(s), such as an amino and/or carboxyl terminal cysteine, if so desired) can readily be synthesized either using an automated DNA synthesizer (e.g., Oligo 1000 DNA Synthesizer, Beckman Corp.) or by contracting with a commercial DNA synthesizing service (e.g., Genset Corp., La Jolla, Calif.). The synthesized DNA molecule can then be inserted into any of a variety of available gene expression systems (e.g., bacterial plasmids; bacteriophage expression vectors, retroviral expression vectors, baculoviral expression vectors), using standard methods available in the art (e.g., Sambrook et al., *Molecular Cloning: A Laboratory Manual* Vols. 1–3 (Cold Spring Harbor Laboratory, Cold Spring Harbor, N.Y., 1989)) and/or as directed by the manufacturer of a particular commercially available gene expression system (e.g., pPROEX™-1 bacterial cell expression system; SFV eukaryotic cell expression system; BAC-TO-BAC™ baculovirus expression system; Life Technologies, Inc., Gaithersburg, Md.). The expressed peptide is then isolated from the expression system using standard methods to purify peptides. Purification of the peptides of this invention may be expedited by employing affinity chromatography or immunoprecipitation based on using antibodies to the particular helper T cell epitope or B cell epitope (CETP-related portion) amino acid sequence of a vaccine peptide of this invention. For example, the Mab TP2 binds to the carboxyl terminal 26 amino acids of human CETP, and could be useful in one or more immunoaffinity steps in a purification scheme (Hesler, C. B., et al., *J. Biol. Chem.*, 263: 5020–5023 (1988)).

In a preferred embodiment, a peptide of this invention also contains an amino terminal cysteine residue, or other residue, covalently linked to the amino terminal amino acid of the helper T cell epitope portion of the vaccine peptide of this invention for use in tethering or coupling the peptide to itself to form dimers of vaccine peptides or to other molecules, such as carrier or cross-linker molecules. Most preferably, the vaccine peptide of this invention has the amino acid sequence C Q Y I K A N S K F I G I T E F C F P E H L L V D F L Q S L S (SEQ ID NO:2).

D. Production of Vaccine Compositions

The peptides of this invention are used to make vaccines that elicit production of endogenous antibodies which specifically bind to CETP and/or modulate (i.e., decrease or inhibit) endogenous CETP activity. The compositions for anti-CETP vaccines of this invention may contain one or several different peptides of this invention. For example, peptides having different helper T cell epitope portions (e.g., different universal helper T cell epitopes) and/or different B cell epitope portions (e.g., different CETP-related portions of the carboxyl terminal 26 amino acids of CETP) may be combined and administered as a single vaccine composition.

Pharmaceutically acceptable adjuvants, such as alum, may be mixed with vaccine peptides of this invention. Alum is the single adjuvant currently approved for use in administering vaccines to humans (see, Eldridge, J. H., et al., In *Immunobiology of Proteins and Peptides V: Vaccines: Mechanisms, Design, and Applications*, Atassi, M. Z., ed. (Plenum Press, New York, 1989), page 192). Recently, alum was used in combination with a sodium phthalyl derivative of lipopolysaccharide to administer a vaccine shown to be effective against human chorionic gonadotropin to humans (see, Talwar, G. P., et al., *Proc. Natl. Acad. Sci. USA*, 91: 8532–8536 (1994)).

Other conventional adjuvants may be used as they are approved for a particular use. For example, biodegradable microspheres comprised of poly (DL-lactide-co-glycolide) have been studied as adjuvants for oral or parenteral administration of vaccine compositions (Eldridge, J. H., et al., In *Immunobiology of Proteins and Peptides V: Vaccines: Mechanisms, Design, and Applications*, Atassi M. Z., ed. (Plenum Press, New York, 1989), pp. 191–202).

Other adjuvants have been used for administering vaccines to non-human mammals. For example, Freund's Complete Adjuvant (Sigma Chemical Co., St. Louis, Mo.), Freund's Incomplete Adjuvant (Sigma Chemical Co., St. Louis, Mo.), and the RIBI™ Adjuvant System (RAS; RIBI ImmunoChem Research, Inc., Hamilton, Mont.) are well known adjuvants routinely used to administer antigens to animals other than humans. In addition, adjuvant structures may also be mixed with or, preferably, covalently incorporated into peptides of this invention, for example at the amino or carboxyl terminal amino acid residue of the peptides. Such incorporated adjuvants include lipophilic N-palmitoyl-S-[2,3-bis(palmitoyloxy)propyl)]-cysteine ("Pam$_3$-Cys-OH") at the amino terminus of the peptides of this invention; amphiphilic, water-soluble lipopeptide such as (i.e., Pam$_3$-SEQ ID NO:4) and Pam$_3$-Cys- Ser-Glu$_4$ i.e., Pam$_3$-SEQ ID NO:5); glycopeptides such as N-acetyl-glucosaminyl-N-acetylmuramyl-alanyl-D-isoglutamine ("GMDP"), muramyl dipeptides, and alanyl-N-adamantyl-D-glutamine; and polyamide gel-based adjuvants which can easily be attached to peptides during their in vitro chemical synthesis (see, *Synthetic Vaccines*, Nicholson, B. H., ed. (Blackwell Scientific Publications, Cambridge, Mass., 1994), pp. 236–238).

In addition, the vaccine peptides of this invention may be linked to other molecules that may enhance the immunogenicity of the peptides. For example, linking peptides of this invention to a surface of a larger molecule, such as serum albumin, may enhance immunogenicity because the epitopes of the vaccine peptides are presented to the immune system of an individual as adjacent multiple repeated copies (see, e.g., Tam, J. P., *Proc. Natl. Acad Sci. USA*, 85: 5409–5413 (1988); Wang, C. Y., et al., *Science*, 254: 285–288 (1991); Marguerite, M., et al., *Mol. Immunol.*, 29: 793–800 (1992)). Such "multiple" or "multivalent" arrangements of the vaccine peptides of this invention can be created using cross-linker molecules (see above). For example, as noted above, bifunctional cross-linker molecules possess two reactive sites, one of the sites can attach the linker to a vaccine peptide of this invention and the other site is available to react with a different molecule, e.g., a larger protein like serum albumin or a resin or polymeric bead. Thus, covalent cross-linker molecules may be used to link vaccine peptides to other proteins or substrates to form multicopy arrangements of the peptides (multicopy peptide assemblies). Linking vaccine peptides of this invention to another molecule or surface should be carried out in a manner that does not significantly disrupt or reduce the immunogenic characteristics of the linked helper T cell epitope and B cell epitope (CETP-related) portions of the vaccine peptides. Preferably, the use of such linker molecules enhances the immunogenicity of the vaccine peptides of this invention as evidenced, for example, by a more rapid rise in anti-CETP antibody titer and/or production of higher affinity anti-CETP antibodies than when individuals are administered vaccine peptides that are not linked. Such cross-linker molecules may also be used to attach a peptide of this invention to an "immunogenic enhancer" molecule such as granulocyte-macrophage colony-stimulating factor (GM-CSF), which was been shown to serve as an effective immunogenic enhancer in generating the production of specific anti-tumor antibodies (e.g., Tao, M. H., et al., *Nature*, 362: 755–758 (1993)). Another such immunogenic enhancer is keyhole limpet hemocyanin (KLH) (see, Ada, G. L., In *Fundamental Immunology third edition*, W. E. Paul, ed. (Raven Press Ltd., New York, 1993), pp. 1309–1352).

2. Use of Vaccine Peptides

General methods of administering and testing vaccines are well known to those skilled in the art (see, e.g., Talwar, G. P., et al., *Proc. Natl. Acad. Sci. USA*, 91: 8532–8536 (1994)). The peptides of this invention are specifically designed to be administered, either alone or in association with one or more pharmaceutically acceptable carriers or adjuvants, as a vaccine which will elicit an antibody response against endogenous CETP of the vaccine recipient. In some embodiments of this invention, the vaccine peptides may also be combined and administered with vaccines for other diseases or disorders. The immune response to endogenous CETP should significantly inhibit CETP activity, and thereby produce a change in the circulating levels of LDL and/or VLDL and/or HDL. Control of LDL, VLDL and/or HDL levels is an accepted indicator or endpoint in treatment of cardiovascular disease as these levels are correlated with a decreased risk of cardiovascular disease or further progression of such disease (Mader, S. S., In *Human Biology*, 4th ed., pp. 83, 102 (Wm. C. Brown Publishers, Dubuque, Iowa, 1995)). Accordingly, the desired prophylactic or therapeutic effect according to this invention is evidenced by eliciting antibodies in an individual that bind to CETP and/or inhibit CETP activity, or by a relative decrease in LDL and/or VLDL levels compared to HDL levels as the titer of antibody directed against the endogenous CETP rises, or by an elevation of absolute levels of circulating HDL with the production of anti-CETP antibodies.

Such endogenously produced antibodies against an individual's own CETP is advantageous over other possible therapeutic approaches. For example, use of polypeptide inhibitors of CETP, such as one recently isolated from baboons (see, e.g., WO 93/11782; Kushwaha, R. S., et al., *J. Lipid Res.*, 34: 1285–1297 (1993); *Genetic Engineering News*, 14: 44 (1994); *Science*, 262: 1974–1975 (1993)), or infusion of exogenously produced (foreign) anti-CETP-antibodies which inhibit CETP activity, are both likely to elicit an immune reaction directed against such foreign CETP inhibitory molecules. Such an immune response could rapidly inactivate and/or clear from the body the exogenously supplied CETP inhibitor. Theoretically, such an immune response against the exogenously supplied CETP inhibitor could be overcome by administering increasing doses of the inhibitor. However, multiple administrations of doses of a foreign CETP inhibitor, particularly multiple doses of ever-increasing amounts of such foreign molecules, presents the possibility of a hypersensitivity reaction, endangering the health of the individual being treated. Such problems associated with using exogenously produced CETP inhibitors are avoided by using the peptide-based vaccines of this invention, which recruit an individual's own immune system antibodies to specifically inhibit endogenous CETP. Repeated dosing, graduated dosing, and undesirable side-effects (such as HAMA response) are avoided by employing the anti-CETP vaccine approach described herein.

The CETP vaccine peptide compositions of this invention may be administered by any route used for vaccination, including: parenterally such as intraperitoneally, interperitoneally, intradermally (subcutaneously), intramuscularly, intravenously or orally. Preferably, the vaccines of this invention are administered parenterally, e.g., intraperitoneally, interperitoneally, intradermally, intramuscularly, or intravenously. If oral administration of a vaccine peptide is desired, any pharmaceutically acceptable oral excipient may be mixed with the vaccine peptides of this invention, for example, such as solutions approved for use in the Sabin oral polio vaccine. As with certain other vaccines, such as for tetanus, an occasional booster administration of the CETP vaccine peptide compositions may be necessary to maintain a desired level of modulation or inhibition of endogenous CETP. As noted above, biodegradable microspheres, such as those comprised of poly (DL-lactide-co-glycolide), have been shown to be useful for effective vaccine delivery and immunization via oral or parenteral routes (Eldridge, J. H., et al., In *Immunobiology of Proteins and Peptides V: Vaccines: Mechanisms, Design, and Applications*, Atassi, M. Z., ed. (Plenum Press, New York, 1989), pp. 191–202).

Appropriate dosages of the peptide vaccines of this invention are established by general vaccine methodologies used in the art based on measurable parameters for which the vaccine is proposed to affect, including monitoring for potential contraindications, such as hypersensitivity reaction, erythema, induration, tenderness (see, e.g., *Physician's Desk Reference*, 49th ed., (Medical Economics Data Production Co., Mont Vale, N.J., 1995), pp. 1628, 2371 (referring to hepatitis B vaccine), pp. 1501, 1573, 1575 (referring to measles, mumps, and/or rubella vaccines), pp. 904, 919, 1247, 1257, 1289, 1293, 2363 (referring to diphtheria, tetanus and/or pertussis vaccines)); Talwar, G. P., et al., *Proc. Natl. Acad. Sci. USA*, 91: 8532–8536 (1994)). A common and traditional approach for vaccinating humans is to administer an initial dose of a particular vaccine to sensitize the immune system and then follow up by one or more "booster" doses of the vaccine to elicit an anamnestic response by the immune system that was sensitized by the initial administration of the vaccine (vaccination). Such a "primary and booster" administration procedure has been well known and commonly used in the art, as for example, in developing and using measles, polio, tetanus, diphtheria, and hepatitis B vaccines.

Initially, the amount of a vaccine peptide administered to an individual may be that required to neutralize the approximate level of endogenous CETP activity present in the individual prior to vaccination, as can be determined by measuring CETP activity in serum or plasma samples from the individual, for example as determined using a commercially available CETP assay (e.g., Diagnescent Technologies, Inc., Yonkers, N.Y.). Plasma or serum samples from a vaccinated individual can also be monitored to determine whether a measurable increase in the levels of total HDL or HDL-C is seen after administration of the vaccine peptide using commercially available assays (e.g., available from Wako Chemicals USA, Inc., Richmond, Va.). A rise in the concentration (titer) of circulating anti-CETP antibodies can be measured in plasma or serum samples, for example using an ELISA assay (see, e.g., Example 3). Thus, it is possible and recommended that initially it be established whether a rise in anti-CETP antibody can be correlated with an increase in the level of HDL or HDL-C, or with a decrease in CETP activity. Thereafter, one need only monitor a rise in titer of anti-CETP antibody to determine whether a sufficient dosage of vaccine peptide has been administered or whether a "booster" dose is indicated to elicit an elevated level of anti-CETP antibody. This is the common procedure with various established vaccinations, such as vaccination against hepatitis B virus.

A more complete appreciation of this invention and the advantages thereof can be obtained from the following non-limiting examples.

EXAMPLE 1

Design and Synthesis of an Anti-CETP Vaccine Peptide

To investigate the possibility of eliciting an antibody response against endogenous CETP, a peptide was prepared having a helper T cell epitope portion comprising a universal tetanus toxoid helper T cell epitope and a B cell epitope portion comprising a carboxyl terminal region of human CETP. A 31-amino acid peptide was designed having the amino acid sequence C Q Y I K A N S K F I G I T E F G F P E H L L V D F L Q S L S (SEQ ID NO:2), in which Q Y I K A N S K F I G I T E (amino acids 2 to 15 of SEQ ID NO:2) is the same amino acid sequence as amino acids 830 to 843 of the tetanus toxoid protein, F G F P E H L L V D F L Q S L S (amino acids 16 to 31 of SEQ ID NO:2) is the same amino acid sequence as amino acids 461 to 476 containing the neutral lipid transfer domain of human CETP and known to be recognized by anti-human CETP Mab TP2 (Wang, S., et al., *J. Biol. Chem.*, 267: 17487–17490 (1992); Wang, S., et al., *J. Biol. Chem.*, 268: 1955–1959 (1993)), and the amino terminal cysteine (C) residue is present for use in linking the peptide to itself or other molecules if desired. The CETP-related portion of this synthetic peptide differs from the corresponding portion of rabbit CETP amino acid sequence only at the glutamic acid (E) residue (see, Nagashima, M., et al., *J. Lipid Res.*, 29: 1643–6149 (1988) (cloning of rabbit CETP gene)). However, prior study has indicated anti-human CETP Mabs can recognize this corresponding region of rabbit CETP (see, Hester, C. B., et al., *J. Biol. Chem.*, 263: 5020–5023 (1988)). The peptide was synthesized to order using standard peptide synthesis methods by Quality Controlled Biochemicals, Inc. (Hopkinton, Mass.).

EXAMPLE 2

Immunization of Rabbits Against Endogenous CETP

The synthetic vaccine peptide (SEQ ID NO:2) of Example 1 above was injected into New Zealand White Rabbits to test the ability of the vaccine peptide to elicit an immune response against endogenous rabbit CETP. Group I contained three rabbits (rb#1–#3), each of which was subjected to a protocol for administration of the vaccine peptide. Group II contained one rabbit (rb#4) as a control that was not treated.

The general protocol for testing the vaccine peptide in the rabbits is shown in FIG. 1. On Day 1, peptide (100 μg) was suspended in the REBI™ adjuvant system (RIBI ImmunoChem Research, Inc., Hamilton, Mont.) according to manufacturer's instructions to a final volume of 1000 μl, and each rabbit of Group I was injected at two intramuscular sites (250 μl per site), subcutaneously at two sites (100 μl per site), and six intradermal sites (50 μl per site). On Day 28, a boost (100 μg of peptide in RIBI™ adjuvant system) was administered as on Day 1. On Day 56, another boost (100 μg of peptide in RIBI™ adjuvant system) was administered as on Day 1.

Blood samples (approximately 1–5 ml) were withdrawn from the ear of each rabbit prior to each initial injection ("prebleed") and on Days 42 and 70, except for control rabbit rb#4. Blood plasma samples were prepared by standard centrifugation methods to separate cellular components from the plasma. Plasma samples were stored at −70° C. Plasma samples of both Groups I and II were analyzed for presence of and increase in titer of anti-CETP antibodies and for total plasma cholesterol and plasma HDL-C levels.

EXAMPLE 3

Figure 2:
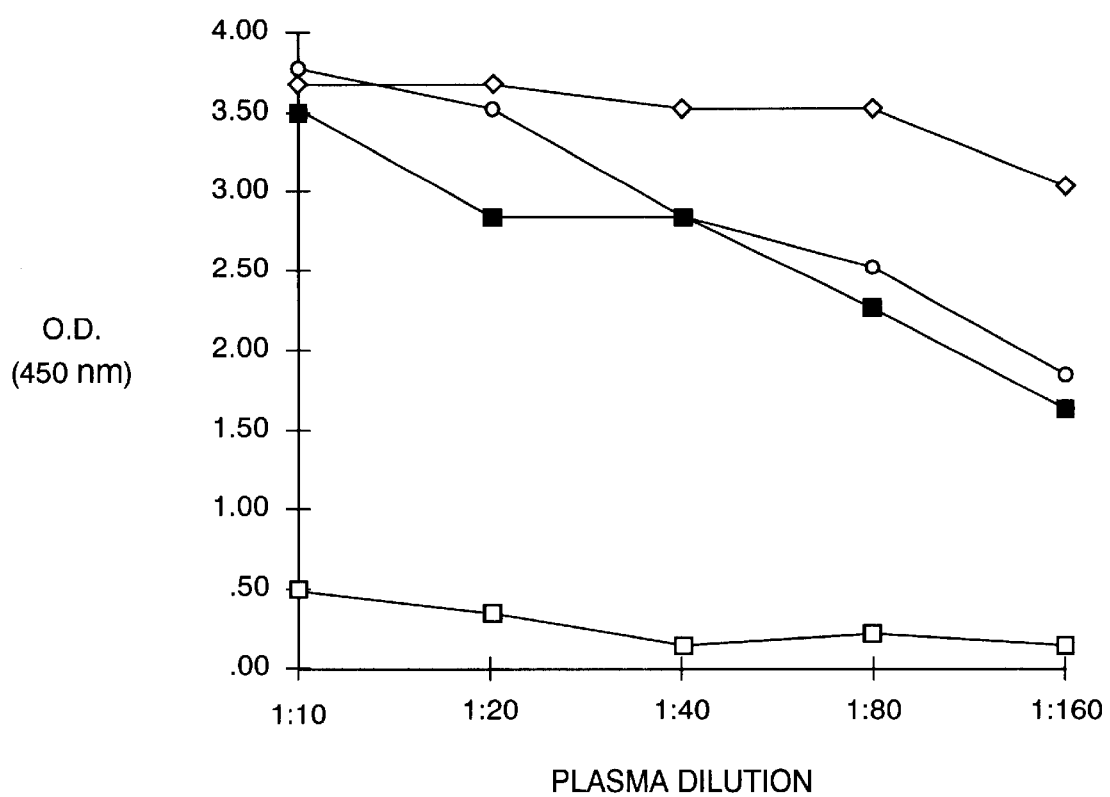
FIG. 2. Optical density (O.D.) at 450 nm versus plasma dilution based on ELISA for anti-CETP antibody binding to recombinant CETP in diluted plasma samples taken from rabbits (rb#1–#4) on Day 70. Open square (rabbit rb#4) refers to the plasma of a rabbit not administered the vaccine peptide (control). Solid square, circle, and diamond refer to rabbits rb#1, #2, and #3, respectively, which were administered a vaccine peptide having the amino acid sequence of SEQ ID NO:2.

Production of Anti-CETP Antibody in Vaccinated Rabbits Direct ELISA for Titering Anti-CETP Antibodies A sandwich enzyme-linked immunosorbent assay (ELISA) was used to titer plasma samples containing anti-CETP antibody. In this set-up, recombinant human CETP (human rCETP, obtained from recombinant CHO cell line CHO(AT) licensed from The Trustees of Columbia University, New York, N.Y.) was adsorbed to wells of a microtiter dish, and various dilutions of rabbit plasma from the rabbits of Groups I and II were added to each well. Each well of a NUNC Maxisorb 96-well plate was coated by overnight exposure at 4° C. to 100 µl of a 1 µg/ml solution of human rCETP in PBS. Non-specific binding was blocked by adding a 1% solution of BSA in PBS and 0.05% Tween to each well and incubating for 2 hours at room temperature (20°–22° C.) on a rotating shaker at 150 rpm The wells were then washed four times with ELISA wash buffer (PBS+ 0.05% Tween). Plasma samples were then diluted 1:10 in dilution buffer (1% BSA in PBS), followed by 6 two-fold serial dilutions in the same buffer. Diluted samples (100 µl) were added to the wells, incubated for 2 hours at room temperature on a rotating shaker at 150 rpm, and then washed 4 times with ELISA wash buffer (PBS +0.05% Tween). To detect bound anti-CETP antibodies, 100 µl of a 1:10,000 dilution of horseradish peroxidase (HRP) labeled goat anti-rabbit immunoglobulin (Southern Biotechnology Associates, Inc.; Birmingham, Ala.) in dilution buffer was added, and the plates were incubated for 2 hours at room temperature on a rotating shaker at 150 rpm. The wells were then washed four times with ELISA wash buffer (see above), peroxidase substrate TMB (TMB peroxidase substrate, Kirkegaard & Perry Laboratories, Inc., Gaithersburg, Md.) added, and the plates were incubated 30 minutes at room temperature. Change in optical density was monitored spectrophotometrically at 450 nm using an ELISA reader (e.g., E-MAX, Molecular Device Corp., Menlo Park, Calif.). In this assay, the O.D. was directly proportional to the amount of anti-CETP antibodies present in the plasma samples. The results indicated that all of the rabbits (rb#1–rb#3) of Group I produced anti-CETP antibody which was specific for recombinant human CETP. No anti-CETP antibody was produced in the untreated control rabbit (rb#4) of Group I in Example 2. See FIG. 2.

Competitive ELISA for Detecting Anti-CETP Antibody

This assay was designed to determine if the vaccinated rabbits had generated antibodies that bind to the same epitope as the anti-CETP Mab TP2 (licensed from The Trustees of Columbia University, New York, N.Y.). A standard competitive ELISA was adapted to detect the presence of anti-CETP antibodies in rabbit plasma. In this assay, horseradish peroxidase (HRP) was conjugated to the anti-CETP Mab TP2 which specifically binds to the 26 amino acid carboxyl terminal fragment of human CETP (Wang et al., J. Biol. Chem., 267: 17487–17490 (1992); Wang et al., J. Biol. Chem., 268: 1955–1959 (1993)).

The following method was used to conjugate HRP to antibody. Antibody was dialyzed against $Na_2CO_3$ (50 mM, pH 9.5). The dialyzed antibody was at a concentration of 2 to 5 mg/ml. HRP (Boehringer-Mannheim) was dissolved in sodium acetate buffer (1.0 mM, pH 4.4) to a concentration of 6 mg/ml. The HRP was then activated by adding 0.2 ml of sodium periodate (21.4 mg/ml acetate buffer, made immediately before use) to every 1 ml of HRP solution, and the activation mixture was incubated at room temperature on a rocker for 20 minutes. The activated HRP was then passed over a G25 column equilibrated with acetate buffer to desalt the activated HRP. An optical density (O.D.) at 403 nm corresponds to approximately 1 mg HRP/ml. The desalted, activated HRP was then added to the dialyzed antibody at an amount equal to one half the amount of antibody (by weight, for example, for every 1 mg of IgG, add 0.5 mg activated HRP), and the mixture was incubated for 2 hours at room temperature on a rocker to allow the HRP to conjugate to the antibody molecules. The conjugation reaction was stopped by adding 20 µl of sodium borohydride (10 mg/ml) for every 1 ml of the HRP-antibody conjugation mixture, and the mixture was then incubated on ice for 30 minutes. The HRP-conjugated antibody mixture was dialyzed overnight against phosphate buffered saline (PBS) and then centrifuged (Airfuge) for 15 minutes at 30 psi. Thimerosal was added to the supernatant (HRP-conjugated antibody) to 0.5%, and bovine serum albumin was added to 1%. The HRP-conjugated antibody preparation was stored at 4° C. and protected from light.

Wells of 96-well microtiter plate were coated with CETP by incubating in each well 100 µl of a 300 ng/ml solution of recombinant human CETP (obtained from the recombinant CHO cell line CHO(AT), licensed from The Trustees of Columbia University, New York, N.Y.) in phosphate buffered saline (PBS). The wells were drained and the wells were filled with a 1% (wt/wt) solution of bovine serum albumin (BSA) in PBS and 0.05% (vol./vol.) Tween (Sigma Chemical Co., St. Louis, Mo.) and incubated for 2 hours at room temperature on a rotating shaker (approximately 150 rpm) to block non-specific binding. The wells were washed four times with ELISA wash buffer (PBS+0.05% Tween), and 100 µl of plasma samples diluted in dilution buyer (1% BSA in PBS) was added. The plates were then incubated for 1 hour at room temperature on a rotating shaker as above, and then washed four times with ELISA wash buffer. To each well was next added 100 µl of a 1:100,000 dilution of horseradish peroxidase-conjugated (labeled) Mab TP2 in dilution buffer. The plates were incubated for 1 hour at room temperature on a rotating shaker as above, then washed four times with ELISA wash buffer. The horseradish peroxidase substrate (e.g., TMB peroxidase substrate, Kirkegaard & Perry Laboratories, Inc., Gaithersburg, Md.) was added to each well and a change in optical density (O.D.) at 450 nm was monitored spectrophotometrically using an ELISA reader (e.g., E-MAX, Molecular Devices Corp., Menlo Park, Calif.). In this assay, if antibody was produced against the CETP-related portion of the vaccine peptide, such unlabeled anti-CETP antibody molecules present in the plasma samples competes with the labeled TP2 Mab for binding to the CETP adsorbed on the walls of the wells and an inhibition in color development is observed as the concentration of plasma sample increases (i.e., O.D. is inversely proportional to the amount of anti-CETP antibody present in each plasma sample).

Figure 3:
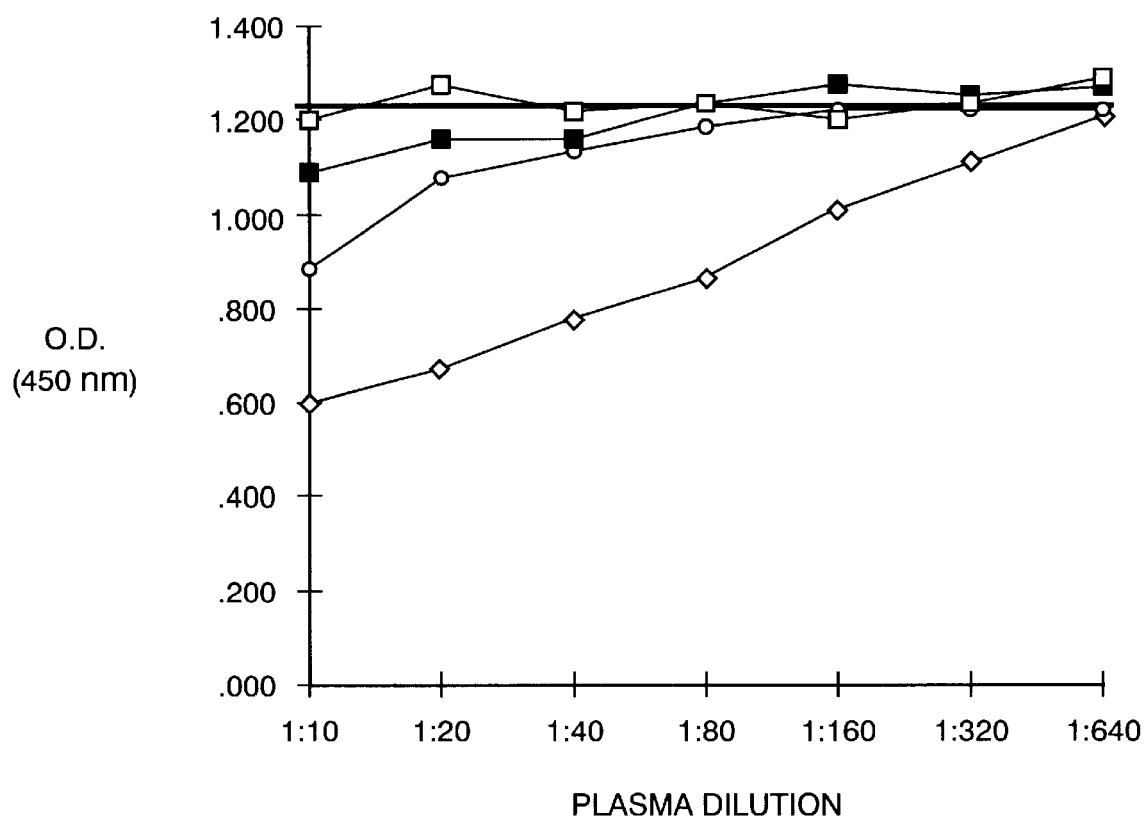
FIG. 3. Optical density (O.D.) at 450 nm versus plasma dilution for blood plasma samples from rabbits (rb#1–#4, see description of FIG. 2, above) based on competitive ELISA for inhibition of monoclonal antibody (Mab) TP2 binding to recombinant human CETP by anti-CETP antibody in diluted rabbit blood plasma samples taken on Day 70.

As shown in FIG. 3, such inhibition of TP2 binding to CETP was observed in plasma sample from two of the three rabbits that were administered the vaccine peptide, thereby indicating production of CETP-specific antibody (compare graphs of rabbit sera rb#2 and rb#3 with plasma of untreated control rabbit rb#4 in FIG. 3). The strongest inhibition of TP2 binding to CETP was exhibited by plasma of rabbit rb#3 (see FIG. 3).

EXAMPLE 4

Cholesterol and HDL Levels in Plasma Samples of Vaccinated Rabbits

Figure 4:
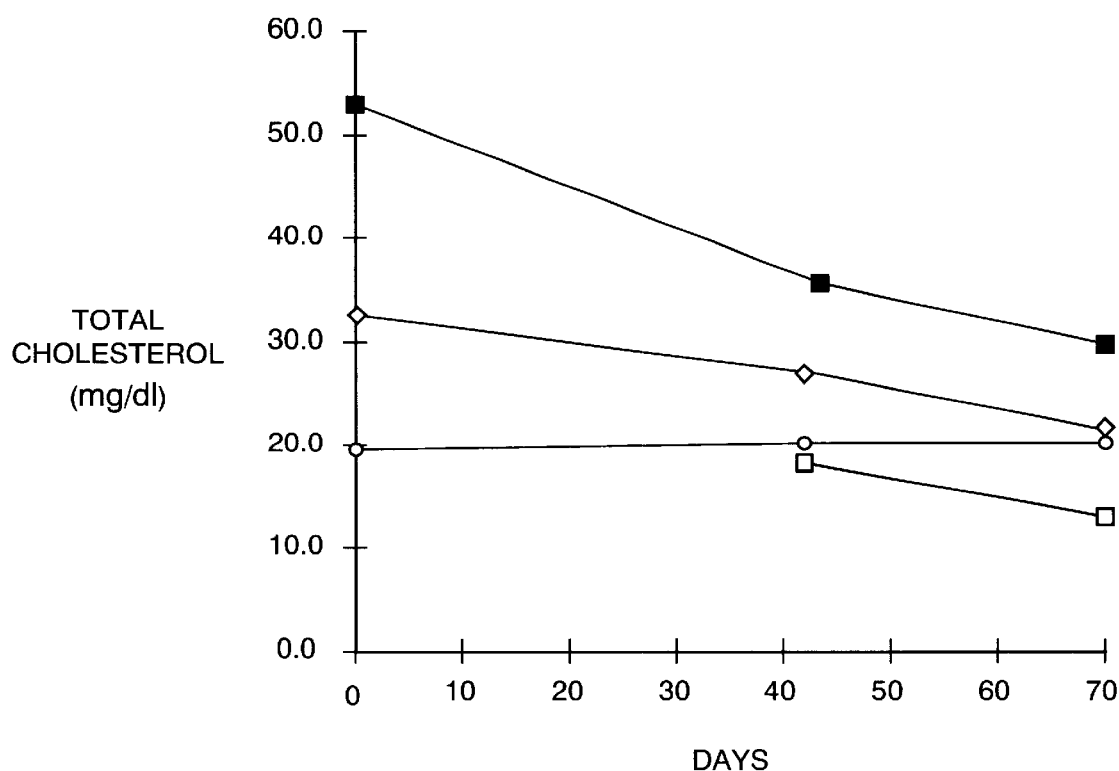
FIG. 4. Concentration of total cholesterol (mg/dl) in plasma samples of rabbits (rb#1–#4, see description of FIG. 2, above) versus time (Days) in vaccination protocol.
Figure 5:
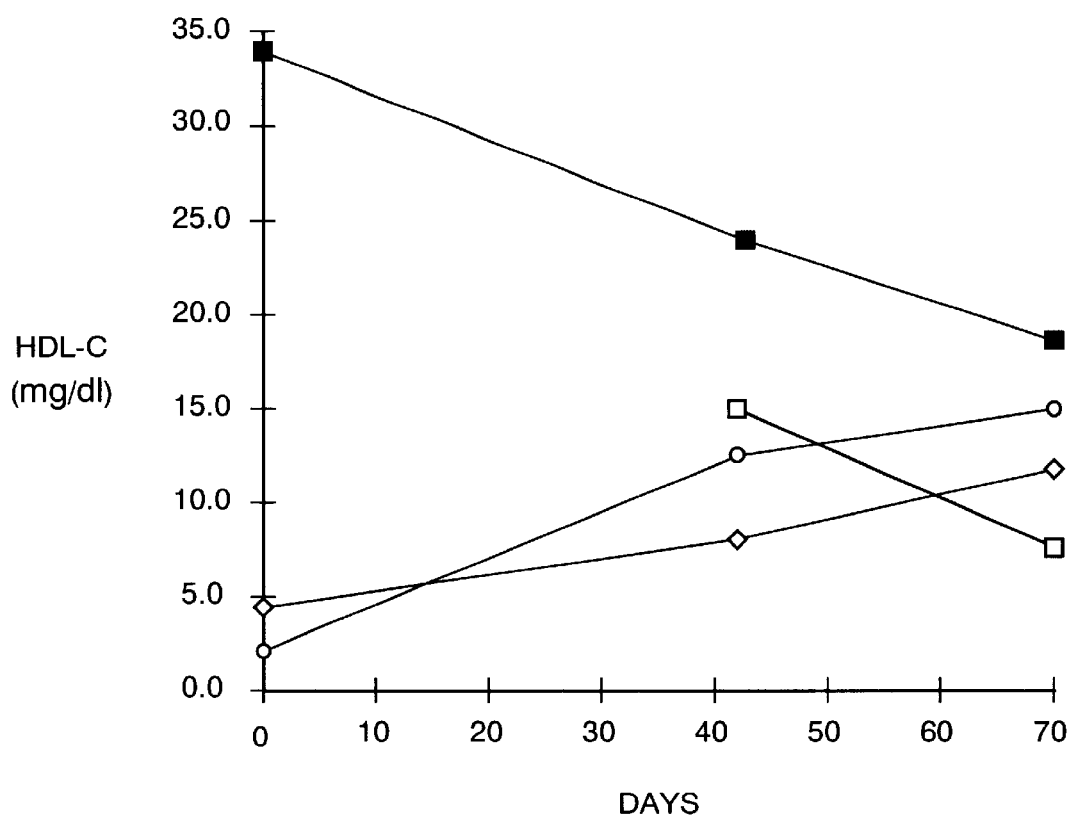
FIG. 5. Concentration of HDL-C (mg/dl) in plasma samples of rabbits (rb#1–#4, see description of FIG. 2, above) versus time (Days) in vaccination protocol.

The plasma samples taken from rabbits of Groups I and II in Example 2 at various times (days) in the vaccination protocol were also assayed for the concentration of total cholesterol (FIG. 4) and HDL-C (FIG. 5). Total plasma cholesterol and HDL-C levels were determined using standard commercial assays (Wako Chemicals USA, Inc., Richmond, Va.). The plasma samples of two rabbits (rb#2 and rb#3) that had the highest anti-CETP antibody titers showed a 2 to 5-fold increase in HDL-C concentrations at Day 70 compared to prebleed plasma samples and compared to the control rabbit (rb#4) and the rabbit (rb#1) with the lowest titer of anti-CETP antibody (FIG. 5).

Although no significant difference in total cholesterol in plasma samples was observed, the ratio of total cholesterol to HDL-C levels generally declined with a rise in anti-CETP antibody levels in the two rabbits (rb#2 and rb#3) of Group I that produced the highest anti-CETP antibody titers in response to the vaccine peptide.

EXAMPLE 5

Administration to Transgenic Mice Expressing Human CETP

A strain of transgenic mice that expresses human CETP has recently become commercially available (BIODIGM-CETP mice; Pharmakon USA, Waverly, Pa.). Such mice express human CETP in their livers and are reported to have approximately 50 percent lower levels of HDL-associated cholesterol than non-transgenic litter mates when fed a normal chow diet. Such transgenic animals serve as an additional experimental model to further test vaccine peptides of this invention.

Two groups consisting of six transgenic CETP-expressing mice were used to test the same vaccine peptide used in Examples 1 to 4 above. Each mouse of Group I received primary injections of the vaccine peptide dissolved in phosphate buffered saline (PBS) and emulsified with complete Freund's adjuvant (1:1) to yield a final concentration of 100 $\mu$g/100 $\mu$l. Each mouse was administered the vaccine peptide mixture in a 50 $\mu$l dose (50 $\mu$g) at each of two subcutaneous sites. On Day 28 and again on Day 56, the animals were similarly administered boosts of the peptide vaccine (100 $\mu$g) in PBS, except the vaccine peptide was emulsified with Incomplete Freund's adjuvant. Samples of blood were withdrawn on Day 42 and Day 63. The mice of control Group II received primary and boost injections of PBS emulsified with adjuvant, but without vaccine peptide, in the same manner as the Group I mice. Plasma samples were prepared as described above for the rabbit plasma samples.

Figure 6:
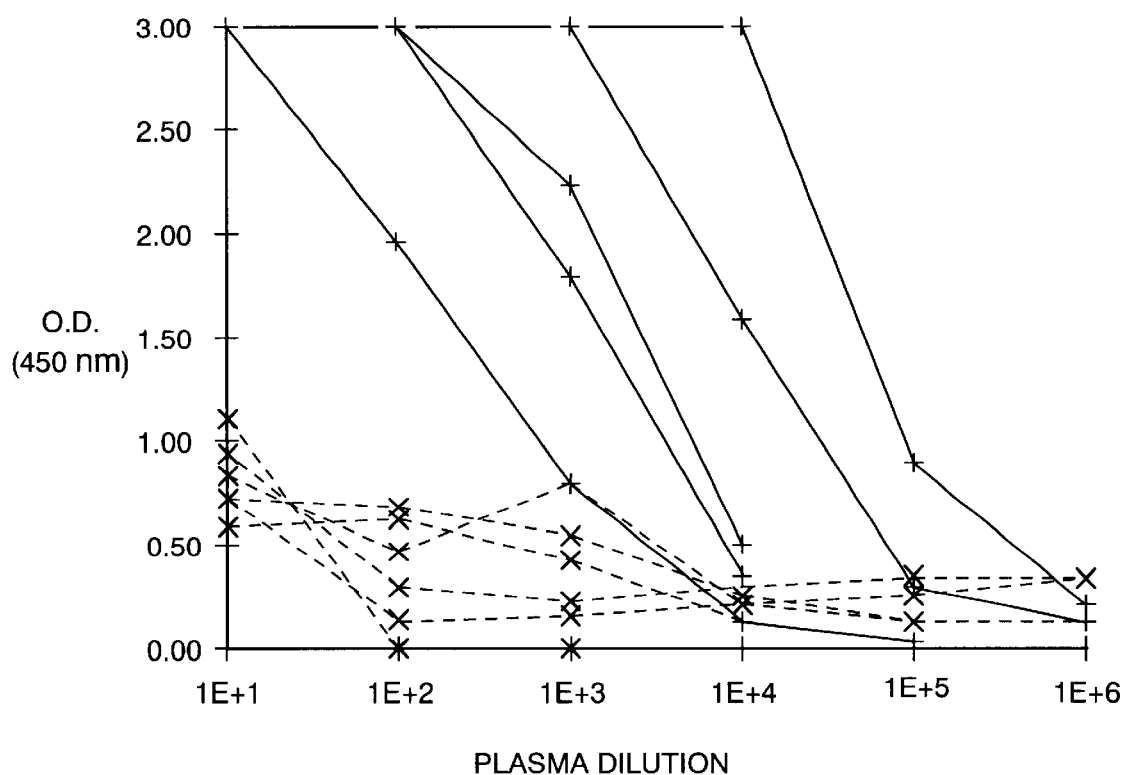
FIG. 6. Optical density (O.D.) at 450 nm versus plasma dilution (semi-logarithmic graph) based on ELISA for anti-CETP antibody binding to recombinant CETP in diluted plasma samples taken from human CETP-transgenic mice on Day 70 in the vaccination protocol. The data for each mouse administered a vaccine peptide having the amino acid sequence of SEQ ID NO:2 is indicated by "+" and a solid line. Data for each control mouse is indicated by "x" and a dashed line. Plasma dilutions spanned a range of 1:10 to 1:1,000,000 (1E+1 to 1E+6).

All Group I mice had significant titers of anti-CETP antibody as measured in a wide range of plasma dilutions (1:10 to 1:1,000,000) by direct ELISA as described above (see FIG. 6). Furthermore, three of the six mice from Group I were also shown to have anti-CETP antibody that competed with Mab TP2 for binding to recombinant human CETP (as was found for rabbits rb#2 and rb#3 in Example 3, above).

Although a number of embodiments have been described above, it will be understood by those skilled in the art that modifications and variations of the described compositions and methods may be made without departing from either the spirit of the invention or the scope of the appended claims. The articles and publications cited herein are incorporated by reference.

I claim:

1. An isolated antigenic hybrid peptide comprising a helper T cell epitope portion linked to a B cell epitope portion, wherein said B cell epitope portion comprises six to 26 consecutive amino acids of the carboxyl terminal 26 amino acids of human cholesteryl ester transfer protein (SEQ ID NO:1).

2. The isolated antigenic hybrid peptide according to claim 1 wherein the helper T cell epitope portion is selected from the group consisting of a helper T cell epitope amino acid sequence of tetanus toxoid, diphtheria toxoid, pertussis vaccine, Bacile Calmette-Guerin (BCG), polio vaccine, measles vaccine, mumps vaccine, rubella vaccine, purified protein derivative of tuberculin, keyhole limpet hemocyanin, and combinations thereof.

3. The isolated antigenic hybrid peptide according to claim 1, wherein the helper T cell epitope portion comprises a helper T cell epitope from tetanus toxoid or diphtheria toxoid.

4. An isolated antigenic hybrid peptide comprising the amino acid sequence of SEQ ID NO:2.

5. The isolated antigenic hybrid peptide according to claim 4 consisting of the amino acid sequence of SEQ ID NO:2.

6. The isolated antigenic hybrid peptide according to claim 4, wherein said isolated antigenic hybrid peptide is a dimer of SEQ ID NO:2.

7. A vaccine composition comprising an antigenic vaccine hybrid peptide comprising a universal helper T cell epitope linked to a B cell epitope portion comprising six to 26 consecutive amino acids of the carboxyl terminal 26 amino acids of human cholesterol ester transfer protein (SEQ ID NO:1).

8. The vaccine composition according to claim 7 wherein the helper T cell epitope portion of the antigenic vaccine hybrid peptide is selected from the group consisting of the amino acid sequence of amino acids 830 to 843 of tetanus toxin protein (amino acids 2 to 15 of SEQ ID NO:2) and the amino acid sequence of amino acids 947 to 967 of tetanus toxin protein (SEQ ID NO:3).

9. The vaccine composition according to claim 7 wherein the T cell epitope portion of the antigenic vaccine hybrid peptide is a universal helper T cell epitope selected from the group consisting of T cell epitope amino acid sequences of tetanus toxoid, diphtheria toxoid, pertussis vaccine, Bacile Calmette-Guerin (BCG), polio vaccine, measles vaccine, mumps vaccine, rubella vaccine, purified protein derivative of tuberculin, keyhole limpet hemocyanin, and combinations thereof.

10. The vaccine composition according to claim 7 wherein the antigenic vaccine hybrid peptide further comprises an amino terminal cysteine residue.

11. A method of elevating the ratio of circulating High Density Lipoprotein to circulating Low Density Lipoprotein, Very Low Density Lipoprotein, or total cholesterol in a human or other animal comprising administering to the human or animal an antigenic vaccine hybrid peptide comprising a universal helper T cell epitope portion and a B cell epitope portion. wherein said B cell epitope portion comprises six to 26 consecutive amino acids of the carboxyl terminal 26 amino acids of human cholesteryl ester transfer protein (SEQ ID NO:1).

12. The method according to claim 11 wherein the helper T cell epitope portion of the antigenic vaccine hybrid peptide is selected from the group consisting of the amino acid sequence of amino acids 830 to 843 of tetanus toxin protein (amino acids 2 to 15 of SEQ ID NO:2) and the amino acid sequence of amino acids 947 to 967 of tetanus toxin protein (SEQ ID NO: 3).

13. The method according to claim 11 wherein the antigenic vaccine hybrid peptide further comprises an amino terminal cysteine residue.

14. A method of decreasing the level of cholesteryl ester transfer protein activity in a human or other animal comprising administering to the human or animal an antigenic vaccine hybrid peptide comprising a helper T cell epitope portion linked to a B cell epitope portion comprising six to 26 consecutive amino acids of the carboxyl terminal 26 amino acids of human cholesterol ester transfer protein (SEQ ID NO:1).

15. The method according to claim 14 wherein the antigenic vaccine hybrid peptide is administered in an amount sufficient to elicit production in said human or other animal of anti-cholesterol ester transfer protein antibodies.

16. A method of increasing the level of circulating High Density Lipoprotein in a human or other animal comprising administering to the human or animal an antigenic vaccine hybrid peptide comprising a helper T cell epitope portion and a B cell epitope portion, wherein said B cell epitope portion comprises six to 26 consecutive amino acids of the carboxyl terminal 26 amino acids of human cholesterol ester transfer protein (SEQ ID NO:1).

17. The method according to claim 16, wherein the helper T cell epitope portion is selected from the group consisting of universal helper T cell epitope amino acid sequences of tetanus toxoid, diphtheria toxoid, pertussis vaccine, Bacile Calmette-Guerin (BCG), polio vaccine, measles vaccine, mumps vaccine, rubella vaccine, purified protein derivative of tuberculin, keyhole limpet hemocyanin, and combinations thereof.

18. A method of treating atherosclerosis in a human or animal comprising administering to the human or animal an antigenic vaccine hybrid peptide comprising a universal helper T cell epitope portion linked to a B cell epitope portion, wherein said B cell epitope portion comprises six to 26 consecutive amino acids of the carboxyl terminal 26 amino acids of human cholesteryl ester transfer protein.

19. The method according to any one of claims 11, 14, 16, and 18, wherein said antigenic vaccine hybrid peptide is a dimer.

20. A method of making an anti-cholesteryl ester transfer protein (CETP) vaccine comprising a B cell epitope portion and a helper T cell epitope portion to modulate endogenous CETP activity, comprising:
    selecting a B cell epitope portion from a region of CETP involved in neutral lipid binding or neutral lipid transfer activity;
    selecting a helper T cell epitope portion consisting of a helper T cell epitope; and
    linking said B cell epitope portion and said helper T cell epitope portion to form a single immunogenic moiety.

21. The method according to claim 20 wherein said B cell epitope portion is covalently linked to said helper T cell epitope portion.

22. The method according to claim 21, wherein said B cell epitope portion is covalently linked to said helper T cell epitope portion via a covalent bond selected from the group consisting of peptide bonds and disulfide bonds.

23. The method according to claim 20 wherein said B cell epitope portion is linked to said helper T cell epitope portion via a cross-linker molecule.

24. The method according to claim 20 wherein said B cell epitope portion is linked to said helper T cell epitope portion via a bridge of amino acids.

25. The method according to claim 20 wherein said B cell epitope portion and said helper T cell epitope portion are linked to a common carrier molecule.

26. The method according to claim 20 wherein said B cell epitope portion is linked to said helper T cell epitope portion to form a vaccine peptide and further comprising the step of linking said vaccine peptide to a carrier molecule.

* * * * *